United States Patent [19]

Amey

[11] Patent Number: 4,599,422

[45] Date of Patent: Jul. 8, 1986

[54] MANUFACTURE OF PYRIDINE

[75] Inventor: Ronald L. Amey, Wilmington, Del.

[73] Assignee: E. I. Du Pont de Nemours and Company, Wilmington, Del.

[21] Appl. No.: 655,087

[22] Filed: Sep. 27, 1984

[51] Int. Cl.$^4$ ............................................. C07D 213/02
[52] U.S. Cl. ..................................... 546/251; 546/250
[58] Field of Search ................................ 546/250, 251

[56] References Cited

U.S. PATENT DOCUMENTS 3,592,817  7/1971  Johnston et al. .................... 546/250
4,294,968  10/1981  Stone et al. ......................... 546/251

FOREIGN PATENT DOCUMENTS 40-23175  10/1965  Japan .................................. 546/250
52-31069  3/1977  Japan .................................. 546/250

OTHER PUBLICATIONS

Bell et al., J. Chem. Soc., (C), 352–354 (1969).

Primary Examiner—Alan L. Rotman

[57] ABSTRACT

A process for the preparation of pyridine by dehydrogenating and cyclizing pentenenitriles.

4 Claims, No Drawings

MANUFACTURE OF PYRIDINE

BACKGROUND OF THE INVENTION

1. Field of the Invention

The present invention is a process for the preparation of pyridine by dehydrogenating and cyclizing pentenenitriles at a temperature in the range of 500°–600° C. in the presence of certain metallic oxides as catalysts.

2. Description of the Prior Art

The manufacture of indole by oxidatively dehydrogenating and cyclizing o-ethylaniline with molecular oxygen in the presence of a catalyst containing at least one of the oxides of molybdenum, vanadium, iron, copper, thallium, indium and chromium is disclosed in Japanese Patent Publication Kokai, No. 52-31069. Molecular oxygen is essential in that reaction. The preparation of pyridine by contacting aliphatic amines or imines at a temperature in the range 400°–600° C. with molecular iodine is disclosed by Bell et al., *J. Chem. Soc., (C)*, 352-4 (1969). It is disclosed that the addition of oxygen and/or use of a basic metal oxide such as calcium oxide, magnesium oxide or barium oxide reduces the requirements for iodine and improves yield.

The preparation of pyridine by the cyclization of 1-cyano-1,3-butadiene using a proton donor catalyst at a temperature in the range 400°–700° C. is disclosed in Japanese Patent Application Publication No. 40-23175.

The preparation of perchloropyridines by the vapor phase reaction of aliphatic nitriles such as 4-pentenenitriles with chlorine is disclosed in U.S. Pat. No. 3,592,817.

The present invention does not require oxygen or a halogen to effect reaction.

SUMMARY OF THE INVENTION

The present invention involves the preparation of pyridine by heating a pentenenitrile, e.g., 2-pentenenitrile, in an inert reaction medium, e.g., nitrogen at a temperature in the range 500°–600° C., preferably 525°–575° C., and in the presence of a catalyst comprising or consisting essentially of one or more of the following oxides: molybdenum oxide, tungsten oxide, zirconium oxide, vanadium pentoxide, cobalt molybdate, nickel molybdate, bismuth molybdate and mixtures of the foregoing. Molybdenum oxide is the preferred catalyst.

DETAILED DESCRIPTION OF THE INVENTION

The starting materials for the present invention are the pentenenitriles, namely cis- and trans-2-pentenenitrile, cis- and trans-3- pentenenitrile, 4-pentenenitrile and mixtures of the foregoing nitriles. It is preferred to employ relatively pure pentenenitriles or mixtures thereof. The presence of certain impurities, e.g., cyclohexane, benzene, adiponitrile or methylglutaronitrile, can adversely affect the reaction by their decomposition on the catalyst surface whereas the presence of normally occurring reaction byproducts, such as valeronitrile or compounds isomeric with pentenenitriles, e.g., 2-methyl-2- and 3-butene-nitriles, do not inversely affect the reaction.

The pentenenitriles are introduced into the system either in a liquid form and then vaporized or vaporized by passing an inert carrier gas through the liquid nitrile before heating the resulting vapor to the reaction temperature. Preferably the pentenenitriles are combined with an inert gas which functions both as a carrier and an inert reaction medium. Suitable gases include nitrogen, argon, and helium. The concentration of pentenenitrile in the feed, i.e., the gas mixture, can vary over a wide range, e.g., from 1–2% to greater than 95% by weight based upon the weight of the mixture at standard conditions, but is usually maintained in the range 5–80% and, preferably, 10–20% by weight on the same basis.

The catalysts employed in the present invention comprise or consist essentially of molybdenum oxide, tungsten oxide zirconium oxide, vanadium pentoxide, cobalt molybdate, nickel molybdate, bismuth molybdate and mixtures thereof. The catalysts can be introduced into the system in powder form but preferably are contained at a concentration of 2–20% on a typical support such as alumina, silica, alumina/silica mixtures and diatomaceous earth. As should be apparent from the foregoing recitation, the catalyst can be a simple oxide such as molybdenum oxide or a complex oxide such as cobalt and bismuth molybdate. Regardless of the form of the catalyst, it is preferred to condition the catalyst prior to reaction in order to remove any residual moisture or other adsorbed species. This conditioning can be accomplished by heating from a period of 5 minutes to several hours at elevated temperatures, e.g., temperature in the range 400°–600° C. while maintaining a blanket of dry, inert gas such as nitrogen over the catalyst.

Organics and carbon deposit on the catalyst during the synthesis reaction and it is necessary to regenerate the catalyst when the activity and selectivity decrease below satisfactory levels. One convenient method for regeneration involves heating the catalyst in an oxidizing atmosphere at or about the temperature of the synthesis reaction until the organics and deposited carbon are removed. Successive regeneration tends to sinter the metal oxide and/or its support (if present) and to decrease the surface area of the catalyst.

The temperature of the reaction must be maintained in the range 500°–600° C. because below the lower end of the temperature range many of the catalysts tend to promote isomerization as the dominant reaction whereas above 600° C. decomposition of the nitriles to low-boiling, short-chain nitriles and to high-boiling oligomers tends to predominate. The preferred temperature range for the catalysts disclosed herein is 525°–575° C.

The following examples are presented to illustrate but not to restrict the present invention. Parts and percentages are by weight unless otherwise noted. The following abbreviations are used:

c2PN=cis-2-pentenenitrile
t2PN=trans-2-pentenenitrile
3PN=3-pentenenitrile
4PN=4-pentenenitrile VN=valeronitrile
MBN=methylbutyronitrile
Pyr=pyridine.

The apparatus employed in the examples consisted of adjustable venturis for metering the gases at standard conditions, a metering pump for the liquid pentenenitrile, a vaporizing tube, a reaction tube and a product condenser-receiver. The metering pump introduced the liquid pentenenitrile into a stream of metered nitrogen following which the mixture was directed to a stainless steel vaporizing tube 30.5 cm long by 0.32 cm in diameter which was heated by a flexible heating tape to a temperature of approximately 300° C. to effect the vaporization of the pentenenitriles. This vapor mixture was then directed via heated lines (to prevent condensation) downflow through the reactor which comprised a stainless steel tube approximately 12.7 cm long with an external diameter of 1.27 cm and an internal diameter of 1.09 cm which was heated by a split furnace to the indicated temperature. The reaction products were directed to a cooled glass tube where the condensate was collected. The products were analyzed by gas chromatography on a 3.05 m by 0.32 cm stainless steel 10% SE-30/80-100 Supelcoport column programmed at 60° for 16 minutes and then a 32° C. increase per minute to 180° C.

Unless otherwise specified, the flow rate through the reactor was maintained at 0.6 ml per hour of pentenenitrile and 2 l per hour of dry nitrogen.

Catalyst was charged to the reactor by pouring the material into the tube one end of which was sealed by a thin layer of quartz wool and a reduction fitting and gently tapping to settle the particulates. After the catalyst was charged, a quartz wool plug was placed in the tube and the tube placed in the split furnace. The parts of the system were then connected. Nitrogen was introduced through the system at approximately 2 l per hour, the split tube furnace was activated and the temperature of the catalyst was increased to approximately 550° C. Unless otherwise indicated, the catalysts were heated for 15–20 minutes at reaction temperature with this nitrogen purge before the pentenenitriles were metered into the nitrogen stream. Unless indicated otehwise, c2PN having a purity of 99.5% with the remainder being mostly 2-methylbutenenitrile was then metered into the nitrogen upstream of the vaporizer which was heated to produce an exit vapor temperature of approximately 300° C. Results are reported in the Table.

EXAMPLE 1

The reaction tube was charged with approximately 8 g of a catalyst which comprised 10% molybdenum oxide on gamma alumina in the form of 0.32 cm tablets. The vapor was maintained at 300° C. and the catalyst (reaction medium) at 500° C. during the one hour period of the run.

EXAMPLES 2–4

Example 1 was repeated except that the temperature was increased to 550° C. for Example 3 and 600° C. for Example 4. The product was analyzed only for pyridine.

EXAMPLE 5

Example 1 was repeated except that the catalyst was heated for 15 hours under nitrogen at a temperature of 550° C. before the pentenenitrile was introduced and the catalyst was maintained at 550° C. Results are reported for the first 30 minutes and hourly thereafter.

EXAMPLES 6–18

Example 1 was repeated using the catalysts identified in the footnotes and variations as noted. Examples 8, 10 and 12 employed a catalyst (reaction) temperature of 500° C. and all other Examples employed a temperature of 550° C. Results are reported for the first 30 minutes and hourly thereafter except for Example 17 which reports hourly results and Examples 24 and 25 which report results for each cycle.

EXAMPLE 19

Example 13 was repeated except that essentially pure 3PN was employed as the starting material.

EXAMPLE 20

Example 13 was repeated except that a starting material containing 62.5% c2PN, 13.1% VN, 19.6% of mixed organics which consisted primarily of cyclohexane and benzene with lesser amounts of 2-methyl-2- and -3-butenenitriles and adiponitrile were employed.

EXAMPLE 21

Example 13 was repeated except that the starting material contained 88% c2PN and 12% mixed organics containing primarily 2-methyl-2-butenenitriles and 2-methyl-3-butenenitrile.

EXAMPLE 22

Example 13 was repeated except that the c2PN was introduced at a rate of 30 ml/hour and nitrogen at a rate of 4 l/hr as a demonstration of deliberate low conversion.

EXAMPLE 23

Example 13 was repeated except that 4PN of essentially 100% purity was employed as the starting material.

EXAMPLE 24

Examples 24 and 25 demonstrate using alternate cycles of pyridine synthesis and catalyst regeneration. Synthesis was conducted for one hour using the catalyst identified in Example 1 following which the pentenenitrile feed was discontinued and after the system was thoroughly purged with nitrogen, 2 l/hr of air heated to a temperature of 550° C. was passed over the catalyst for 30–45 minutes. The system was then purged with nitrogen before the next cycle of synthesis. The products of each cycle were analyzed and are reported in sequence. The conversion for cycles 1–4 was 91, 83, 67 and 67%, respectively.

EXAMPLE 25

Example 24 was repeated except that the catalyst was heated at 550° C. for 15 hours initially and at 550° with 2 l/hr air for 30-45 min. during each regeneration cycle and three cycles were conducted.

TABLE I

| Example No. | Product (% by Weight) | | | | |
|---|---|---|---|---|---|
| | MBN | c2PN | VN | t2PN | Pyr |
| 1 | 17.8 | 7.2 | 20.3 | 12.8 | 11.7 |
| 2 | — | — | — | — | 11 |
| 3 | — | — | — | — | 17.7 |
| 4 | — | — | — | — | 3.0 |
| 5 | — | — | — | — | 39.6 |
| | — | — | 8.8 | — | 22.9 |
| | — | — | 15.0 | — | 14.0 |
| | — | — | — | — | 4.0 |
| | — | — | — | — | 2.0 |
| 6[1] | — | — | — | — | 24 |
| | — | — | — | — | 4 |
| | — | — | — | — | 3 |
| 7[2] | 20 | 21 | — | — | 16 |
| | 23 | 2 | 15 | — | 12 |
| | 19 | 7 | 16 | 10 | 7 |
| 8[1] | 20 | 6 | 17 | 8 | 6 |
| | 23 | 8 | 20 | 12 | 3 |
| | 24 | 13 | 20 | 20 | 0 |
| 9[3] | — | 16 | — | — | 18 |
| | 18 | 6 | 14 | 8 | 10 |
| | 25 | 9 | 8 | 16 | 6 |
| 10[4] | 15 | 17 | 21 | 31 | 7 |
| | 13 | 18 | 16 | 34 | 6 |
| | 13 | 23 | 13 | 40 | 4 |
| 11[4] | 20 | 5 | 30 | 8 | 10 |
| | 14 | 9 | 27 | 17 | 7 |
| | 18 | 13 | 22 | 23 | 5 |
| 12[5] | 20 | 5 | 21 | — | 16 |
| | 20 | 9 | 19 | 11 | 10 |
| | 15 | 14 | 14 | 23 | 4 |
| 13[5] | 15 | — | 8 | — | 25 |
| | 19 | — | 12 | — | 23 |
| | 17 | — | 15 | 10 | 10 |
| 14[6] | 7 | 19.6 | — | 37.1 | 4.6 |
| | 4.1 | 20.6 | — | 36.9 | 4.2 |
| | 3.6 | 22.8 | — | 40.9 | 2 |
| 15[7] | 14.6 | — | 9.9 | — | 17.9 |
| | 19.4 | — | 15.8 | — | 13.7 |
| | 17.5 | 6.5 | 20.2 | 9.3 | 4.0 |
| 16[8] | 1.9 | 35.2 | 8.2 | 14.4 | 8.5 |
| | 1.5 | 27.9 | 6.5 | 14.5 | 6.5 |
| 17[9] | — | 12.9 | — | 38.7 | 19.4 |
| | — | 21.0 | — | 23.2 | 15.9 |
| | — | 26.3 | — | 31.0 | 15.9 |
| | — | 28.9 | — | 36.9 | 11.2 |
| | — | 36.2 | — | 42.7 | 6.9 |
| 18[10] | — | 11.5 | 1.9 | 24.7 | 17.5 |
| | — | 14.5 | 3.0 | 38.3 | 11.3 |
| | — | 16.9 | 3.7 | 44.7 | 5.2 |
| | — | 18.8 | 3.7 | 50.1 | 3.9 |
| | — | 19.7 | 2.6 | 52.6 | 2.2 |
| 19[5] | 7.9 | — | 9.4 | — | 32.5 |
| | 4.7 | — | 6.4 | — | 15.1 |
| 20 | 6.6 | — | 10.8 | — | 11.8 |
| | 14.9 | 22.9 | 13.5 | — | 21.2 |
| | 12.8 | 21.5 | 18.0 | — | 14.0 |
| | 5.2 | 20.7 | 20.3 | 11.4 | 3.1 |
| 21 | 17 | — | 15.3 | — | 26.7 |
| | 16 | 7.5 | 10.2 | — | 14 |
| | 14 | 11.9 | 7 | 24 | 9 |
| 22 | 5.4 | 34 | 8 | 43 | 2 |
| | 18.0 | 14 | 5.3 | 30 | 3 |
| 23 | — | 31.9[11] | — | — | 6.17 |
| | — | 35.3[11] | — | — | 4.80 |
| | — | 44.7[11] | — | — | 4.31 |
| | — | 46.1[11] | — | — | 0.41 |
| | — | 50.1[11] | — | — | 0.20 |
| | — | 52.3[11] | — | — | 0.10 |
| 24 | 6.4 | 2.9 | 13.3 | 6.3 | 14.8 |
| | 5.2 | 5.7 | 12.7 | 11.8 | 11.8 |
| | 2.3 | 10.1 | 12.2 | 22.9 | 10.8 |
| | 3.9 | 9.3 | 11.4 | 19.9 | 12.1 |
| 25 | 6.7 | 0 | 14.6 | — | 33.3 |
| | 4.4 | 4.4 | 10.7 | 7.3 | 38.7 |
| | 4.1 | 7.3 | 9.5 | 9.9 | 36.4 |

Footnotes for Table I
[1]Catalyst - 5% NiO and 10% MoO₃ on γ-Al₂O₃ in the form of 0.48 × 0.32 cm tablets.
[2]Catalyst - 3% Co₂O₃ and 9% MoO₃ on γ-Al₂O₃ promoted with SiO₂ (0.32 cm tablets).
[3]Catalyst - 3-4% MoO₃ on γ-Al₂O₃ in the form of 0.48 × 0.32 cm tablets.
[4]Catalyst - 6% NiO and 19% WO₃ on Al₂O₃/SiO₂ (0.32 cm tablets), (surface area-230 m²/g).
[5]Catalyst - 10% MoO₃ on γ-Al₂O₃ in the form of 0.32 cm tablets (Surface area-160 m²/g).
[6]Catalyst - 98% ZrO and 2% Al₂O₃ in the form of 0.32 cm tablets having a surface area of 50 m²/g and heated for about 12 hours at 400° C. in a nitrogen blanket after charging to reactor.
[7]Catalyst - 10% V₂O₅ and SiO₂/Al₂O₃ (0.32 cm tablets) (surface area-139 m²/g).
[8]Catalyst - Bi₂Mo₃O₂ as a powder.
[9]Catalyst - MoO₃ (99.95%) 325 mesh powder.
[10]Catalyst - 5% MoO₃ on SiO₂.
[11]4PN analysis.

I claim:

1. A process for the preparation of pyridine which comprises heating a pentenenitrile in an inert gas reaction medium at a temperature in the range 500°-600° C. in the presence of a catalyst consisting essentially of a compound selected from the class consisting of molybdenum oxide, tungsten oxide, zirconium oxide, vanadium pentoxide, cobalt molybdate, nickel molybdate, bismuth molybdate and mixtures thereof.

2. The process of claim 1 wherein the inert gas is selected from the class consisting of nitrogen, argon, helium and mixtures of the foregoing.

3. The process of claim 1 wherein the temperature is maintained in the range 525°-575° C.

4. The process of claim 3 wherein the catalyst comprises molybdenum oxide.

* * * * *